(12) United States Patent
Gerardi et al.

(10) Patent No.: US 10,578,585 B1
(45) Date of Patent: Mar. 3, 2020

(54) METHOD AND APPARATUS FOR MONITORING CONTAMINANTS IN A FLUID FLOW

(71) Applicants: Joseph Gerardi, Ithaca, NY (US);
Richard Ingram, Ithaca, NY (US);
Gail Hickman, Ithaca, NY (US)

(72) Inventors: Joseph Gerardi, Ithaca, NY (US);
Richard Ingram, Ithaca, NY (US);
Gail Hickman, Ithaca, NY (US)

(73) Assignee: Innovative Dynamics, Inc., Ithaca, NY (US)

(*) Notice: Subject to any disclaimer, the term of this patent is extended or adjusted under 35 U.S.C. 154(b) by 0 days.

(21) Appl. No.: 15/852,357

(22) Filed: Dec. 22, 2017

Related U.S. Application Data

(63) Continuation of application No. 14/523,815, filed on Oct. 24, 2014, now Pat. No. 9,970,903.

(60) Provisional application No. 62/042,910, filed on Aug. 28, 2014.

(51) Int. Cl.
*G01N 29/032* (2006.01)

(52) U.S. Cl.
CPC ..... *G01N 29/032* (2013.01); *G01N 2291/015* (2013.01); *G01N 2291/02408* (2013.01); *G01N 2291/02433* (2013.01); *G01N 2291/048* (2013.01)

(58) Field of Classification Search
CPC ........... G01N 29/032; G01N 2291/015; G01N 2291/048; G01N 2291/02408; G01N 2291/02433; G01N 29/046
See application file for complete search history.

(56) References Cited

U.S. PATENT DOCUMENTS

| | | | |
|---|---|---|---|
| 4,339,944 A | 7/1982 | Abts et al. |
| 4,381,674 A | 5/1983 | Abts |
| 4,527,420 A | 7/1985 | Foote |
| 5,357,197 A | 10/1994 | Sorkin |
| 5,741,980 A | 4/1998 | Hill et al. |
| 6,205,848 B1 | 3/2001 | Faber et al. |
| 7,288,139 B1 | 10/2007 | Showalter |
| 7,900,507 B2 | 3/2011 | Kauffman |
| 2002/0148408 A1 | 10/2002 | Gompper et al. |

(Continued)

FOREIGN PATENT DOCUMENTS

| | | |
|---|---|---|
| GB | 1012010 | 1/1965 |

OTHER PUBLICATIONS

Du and Zhe "An integrated ultrasonic-inductive pulse sensor for wear debris detection" Journal of Smart Materials and Structures, Published Dec. 21, 2012 (Year: 2012).*

(Continued)

*Primary Examiner* — Peter J Macchiarolo
*Assistant Examiner* — John M Royston
(74) *Attorney, Agent, or Firm* — Randall L. Reed; Miller Mayer LLP

(57) ABSTRACT

An apparatus and method is disclosed to monitor the condition of a fluid flow including particulate matter and air or gas content fluid in the fluid flow as well as fluid quality. The apparatus includes a sensor array with an ultrasonic transducer, inductive sensor and fluid quality sensor. It also includes a cyclonic separator. The method includes sensing and sizing particulate matter, distinguishing air bubbles from the particle matter and assessing the quality of the fluid.

5 Claims, 13 Drawing Sheets

(56) References Cited

U.S. PATENT DOCUMENTS

2002/0196439 A1* 12/2002 Engler ................ G01N 21/532
356/338
2013/0330205 A1  12/2013 Apostolides et al.

OTHER PUBLICATIONS

Du and Zhe, "A high throughput inductive pulse sensor for online oil debris monitoring" Journal of Tribology International, Published Oct. 29, 2010 (Year: 2010).*
Byington, Carl, et al.; An Integrated, Real-Time Oil Quality Monitor and Debris Measurement Cpacity for Drive Tran and Engine Systems; Presented at the American Helicopter Society 66th Annual Form, Phoenix Arizona, May 11-13, 2010.
Edmonds, Jack, et al.; Detection of Precursor Wear Debris in Lubrications Systems; Aerospace Conference Proceedings, 2000 IEEE, Conference Mar. 25-25, 2000.

* cited by examiner

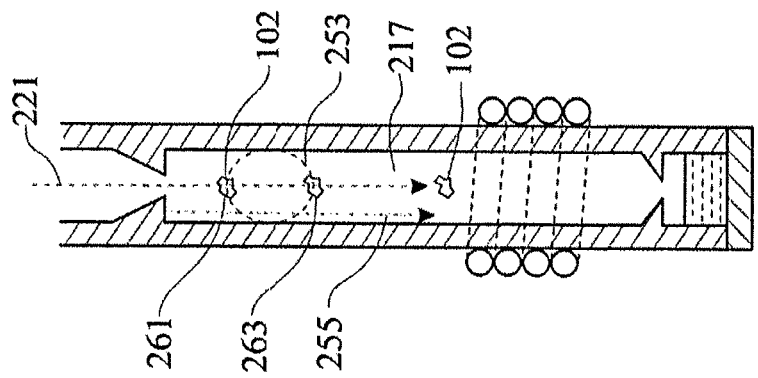
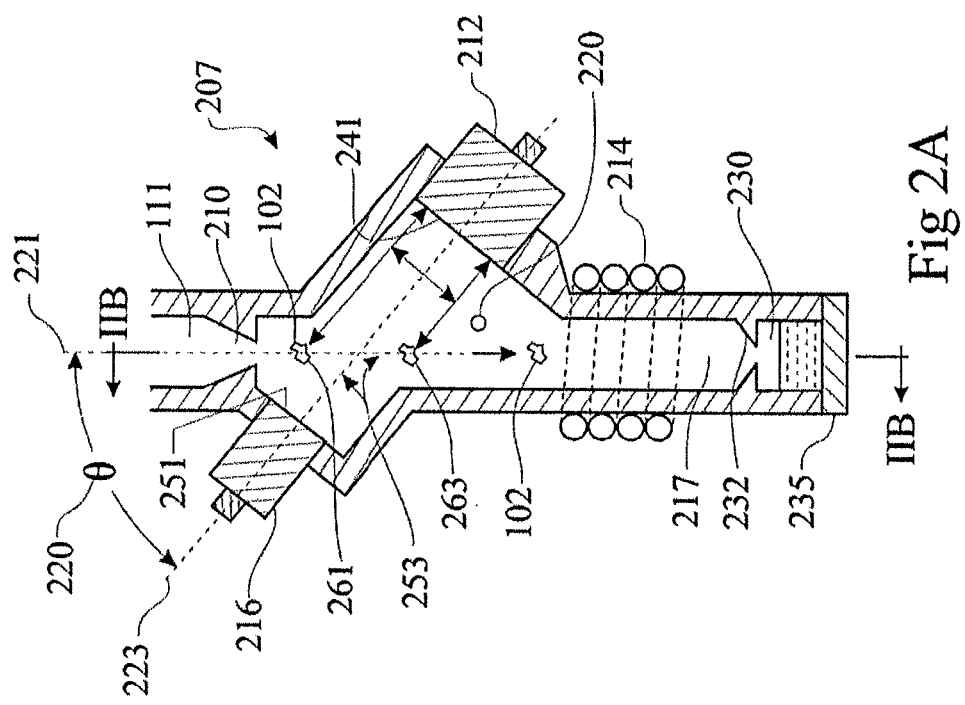
Fig 2A
Fig 2B

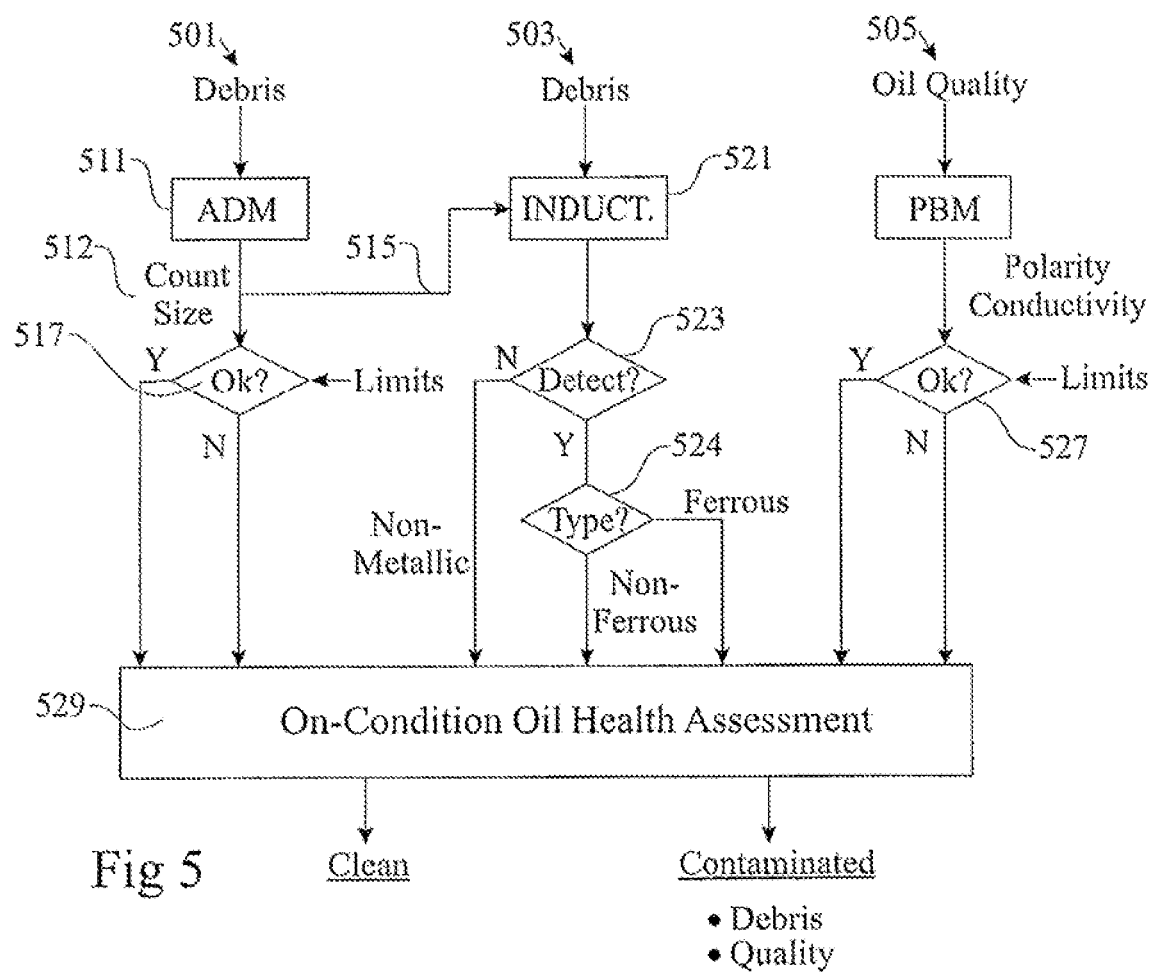

METHOD AND APPARATUS FOR MONITORING CONTAMINANTS IN A FLUID FLOW

This application claims the benefit of priority under 35 U.S.C. § 119 of U.S. Provisional Application Ser. No. 62/042,910 filed on Aug. 28, 2014 entitled "Method and Apparatus for Monitoring Particles in a Fluid Flow", and U.S. patent application Ser. No. 14/523,815 filed Oct. 10, 2014 entitled "Method and Apparatus for Monitoring Particles in a Fluid Flow" the content of both of which are relied upon and incorporated herein by reference in their entirety.

FIELD OF INVENTION

The present invention provides an improved method to enable on-line health monitoring of a fluid circulatory system to determine the condition of the fluid and maximize equipment life. The technologies are based on ultrasonic, inductive and fluid quality sensors and are functionally-integrated into a compact sensing cluster for monitoring the entire fluid flow volume.

BACKGROUND OF INVENTION

Critical machinery increasingly requires that the lubrication system is monitored real-time for indicators of mechanical as well as fluid degradation. Because external factors have an extensive influence on the lubricant during operation, knowing the particle size distribution and material properties of the contamination plus other properties related to lubricant quality such as water saturation, enables the user to evaluate the precise condition of the system. For example, the mechanical components of a helicopter gearbox operate under extreme load, speed and environmental conditions causing rotating component wear that can progress very rapidly to result in a sudden, catastrophic failure. Corrosion precursors, especially water, significantly affect material strength properties in gearbox components, thereby reducing the component's load carrying capacity and ultimately shortening its useful lifetime. Bearing failures often cause reliability issues and can cause catastrophic failures of the entire system. Real time sensors can provide the capability to continuously monitor the lubricant flow to detect the onset of a premature failure and provide for safe shut down. On-line sensors can trend wear debris size and the rate of production as well as identify corrosion precursors. This capability will improve maintenance action and component replacement recommendation, thus increasing asset readiness and reducing total ownership costs.

Engine and gearbox wear is commonly monitored using magnetic chip detectors placed directly in the oil flow that can detect metallic particles approximately 200 μm in size and greater. Inductive sensors are available for detection of both ferrous and non-ferrous metals as well. However, these methods cannot detect non-metallic wear debris particles. This poses a limitation since new high performance engines have begun to utilize new materials and ceramic bearings that offer considerable weight savings, and thus increased fuel efficiency. Obviously, legacy health monitoring systems using magnetic or inductive sensors are not capable of detecting the failures of these non-metallic materials.

Hence there is a need to monitor the health of these non-metallic components. Also, it is desirable to be able to monitor all of the circulating fluid (oil), not just a portion of it, to ensure that all the larger more serious wear debris particles are detected. As a general rule, the larger the particle size, the more serious the potential failure condition, but correspondingly occur more rarely. A sampling strategy is not appropriate to address the rarely occurring larger particles. Thus, all of the oil flow must be monitored; an in-line system for monitoring is the best option. In addition, there is also a need to monitor the lubricant quality such as water saturation which accelerates the aging process of metallic engine components.

Prior art technology does not address all the above requirements. A number of patents and papers relate to acoustic monitoring of fluid flow. A method of this type is disclosed in British Patent 1,012,010 (1963) which describes a method and equipment for counting and measuring particles in various measurement zones along the acoustic axis of an ultrasonic transducer in the suspension. By using suitable time windows when receiving the reflected acoustic signals, the particles in a predetermined number of measurement zones are counted. By making use of a different threshold voltage for each time window, a minimum size for the particles to be counted is selected for each zone. Assuming that the particle distribution is the same in each zone, and only one particle is within the measurement zone, a rough estimate of the number of particles, subdivided according to particle size is obtained.

Other systems characterize the type and shape of particles in the suspension by evaluating the angle-dependent reflection behavior of the particle. U.S. patent Ser. No. 04/381,674 (1983) and 04/527,420 (1985) describe a bistatic arrangement for target material identification on the basis of the ratio of the outputs of two transducers. U.S. patent Ser. No. 04/339,944 (1982) covers particle discrimination on the basis of comparing spectral characteristics of the reflected pulse with previously acquired spectra of known particles. This is also described in Nemarich, C. P., J. C. Tuner, and Whitesel, H. K., "Evaluation of an On-Line Ultrasonic Particle Sensor Using Bearing Test Data", $41^{st}$ Meeting of the Mechanical Failures Prevention Group, Patuxent River, Md. (1986). In U.S. Pat. No. 6,205,848 (2001) a large measurement Volume is described such that the angle of incidence varies as a function of the lateral position. If a particle in the flowing suspension is exposed various times in succession by an acoustic signal, the successive reflection signals differ as a consequence of the angle-dependent reflection.

Prior work using ultrasonic transducers for wear debris measurements performed by Innovative Dynamics Inc. [(1) Edmonds, J., M. Resner, and K. Skharlet, "Detection of precursor wear debris in lubrication systems", IEEE, 2000; (2) Edmonds, J., J. Gerardi, G. Hickman, "Helicopter/Tiltrotor Gearbox Debris Monitoring", Navy SBIR Phase I IDI Final Report, 1995) has shown the ability to measure particles down to 5 um in diameter, and when combined with inductive sensors provides full spectrum wear debris monitoring capability, allowing one skilled in the art to be able to identify and differentiate both metallic and non metallic wear debris particles.

These methods all use focused ultrasonic transducers to estimate the particle concentration and the particle size distribution based on statistical sampling of the flow. These methods are limited by the shape of the acoustic beam and only a partial volume of the fluid that passes by the transducer is monitored. Particles outside the focus region, including larger size particles indicative of impending failure, can therefore not be detected. Also, while some of these methods can differentiate air bubbles and solid particles because they have distinct spectral shapes, these methods do not currently sample fast enough to detect all debris if the flow rate or debris concentration is relatively high, thus requiring complex high speed sampling hardware. Although an ultrasonic transducer responds to all solid debris and current designs are unable to reliably differentiate between metallic debris and non-metallic debris, air bubbles, or water.

SUMMARY OF THE INVENTION

In accordance with the present invention, there is provided a collimated ultrasonic method for the real time monitoring of contaminants in a fluid that is capable of identifying the number and size of debris particles by acoustic means, the type of material by electromagnetic or inductive means and the lubricant quality by capacitance means.

It is another objective of this invention to detect and measure all wear debris particles generated in a system by sampling a representative fluid volume, as opposed to statistical sampling methods that focus on a relatively small sample volume that do not necessarily measure all wear debris particles in the fluid or lubrication system.

It is another objective to determine the basic material type of the debris particle sized from approximately 10 μm and greater in order to determine whether it is metallic (ferrous or nonferrous) or nonmetallic (ceramic) as to infer wear status of all critical internal system components that the lubricant contacts.

It is another objective to provide a means to mitigate the presence of air bubbles in the sensing zone of the ultrasonic sensor and to discern the difference between solid particles and air bubbles as to insure against false positive sensing events.

It is another objective to monitor the lubrication fluid quality to enable on-condition maintenance rather than based on standard interval-based maintenance. Moreover, the fluid is monitored for moisture content and oxidation.

It is another objective to separate out and ultimately collect all wear debris particles above a threshold size (typically 10 μm), and provide an access port to collect them for verification.

It is another objective of the invention to analyze the acoustic signature response of the fluid to record the amplitude of each particle that arises in the flow (typically in the size range of 10 μm and greater) and time stamp each of them.

It is another objective to provide redundancy for particle size estimation, by means of two different sensing technologies (acoustic and inductive), as well as multiple sensor readings (acoustic) of the same particle.

It is another objective to provide a collimated ultrasonic sensor with a field of view wide enough such that multiple sampling events can be performed on a target. Moreover, this would allow the capability to more accurately size the particle and also discern multiple particles following closely in succession. A focused transducer could potentially be used to sense particles significantly smaller than 10 μm; however it has a narrow field of view and therefore could miss particles in the flow.

It is another objective of the invention to use the ultrasonic sensor in conjunction with an inductive sensor to distinguish between metallic (ferrous and non-ferrous) and nonmetallic (ceramic) particles.

It is another objective of the invention to integrate sensors with a cyclonic phase separator to separate debris particles from the flow (the air bubbles remain with the flow) and sequester the particles through a collection port into a sensing module such that contaminant measurements can be sampled at speeds independent of the flow rate.

It is another objective of the invention to merge the technologies of debris monitoring (ultrasonic and inductive sensors) and oil quality monitoring using multi-sensor data fusion techniques such as neural networks or fuzzy logic to enable a comprehensive prognostic health monitoring system. In this approach, multiple sensor data is used along with known trends in lubrication failures to diagnose the oil condition and to predict the remaining useful life of mechanical components such as gears and bearings.

It is another objective of this invention to monitor the particulate distribution of food and beverages such as wine and coffee for quality control purposes.

The inventions described herein accomplish the above and other objects by providing a sensor array for detecting objects in a fluid flow having: a) an ultrasonic sensor with its transmission axis positioned at an oblique angle to an axis of fluid flow with a reflective surface positioned on an opposite side of the axis of the fluid flow in a position normal to the transmission axis of the ultrasonic sensor to thereby reflect transmissions from the ultrasonic sensor back to the ultrasonic sensor and wherein the oblique angle creates a field of view for it to interrogate with a plurality of ultrasonic pulses acoustically reflective objects and determine direction and size; b) an inductive sensor positioned along the axis of fluid flow adjacent the ultrasonic sensor; c) wherein the ultrasonic sensor determines if an object is a solid particles and an air bubble; the inductive sensor determines if a metallic particle is ferrous or none ferrous and both sensors working together identify nonmetallic particles; and d) wherein the ultrasonic sensor distinguishes between solid particles and air bubbles based on orientation of the sensor array to a local gravitational field.

In another aspect of the sensor array the adjacent position of the inductive sensor is along the axis of fluid flow downstream from the ultrasonic sensor. In yet another aspect of the sensor array the axis of fluid flow can be in a downward direction in a gravitational field. In yet another aspect of the sensor array it can include a fluid quality sensor to determine one or more conditions of a fluid in the fluid flow. In yet another aspect of the sensor array the fluid flow can be an oil circulating system and the fluid quality sensor is an oil quality sensor that assess water content and oxidation of the oil. In yet another aspect of the sensor array it can monitor a fluid flow of fluids that circulate: beer, wine, milk, ice cream, water, or soda. In still yet another aspect of the sensor array the oblique angle at which the ultrasonic sensor axis is positioned at can be in an upward facing position with respect to the local gravitational field. In still another aspect of the sensor the oblique angle is an angle between the transmission axis of the ultrasonic sensor and a path of a particle falling through fluid of the fluid flow. In yet another aspect of the invention the sensor array can have an oblique angle that varies from 89° to 0°. In another aspect the sensor array the oblique angle is optimally 45°. In yet another aspect of the invention the sensor array because of its oblique angle to the axis of fluid flow can interrogate particles with multiple pulses.

In yet another aspect of the invention it has an ultrasonic transducer having: a) a first ultrasonic transceiver and a second ultrasonic transceiver; b) positioning structure for holding the first transceiver in relation to the second transceiver so they have congruent transmission and reception paths but are physically and acoustically separated from each other by the positioning structure; c) an acoustic dampening structure connected to the first transceiver and an acoustic dampening structure connected to the second transceiver; and d) a controller functionally connected to the first transceiver and the second transceiver for activating and controlling operation of the first and second transceiver.

In another aspect of the ultrasonic transducer the first transceiver can be disk shaped and the second transceiver can be ring shaped, and the second transceiver can surround the first transceiver. In yet another aspect of the ultrasonic transducer can have a positioning structure holding the first and the second transceiver is an acoustic lens with pockets into which the first and the second transceivers fit. In yet another aspect of the ultrasonic transducer one of the transceivers can be used solely for transmission of ultrasonic pulses and one of the transceivers can be used solely for receiving ultrasonic pulses and the transceiver used solely for transmission has a large acoustic dampening structure attached to it to enhance acoustic dampening and the transceiver used solely for receiving has a smaller acoustic dampening structure attached to it to increase its sensitivity to a received signal. In yet another aspect of the ultrasonic transducer the acoustic dampening structures can have an end distal from the transceiver a shaped surface to deflect ultrasonic pulses.

In another aspect of the invention it provides a cyclonic separator for separating particulate matter from a fluid flow having: a) an interior chamber in a shape of a truncated conic section, the truncated conic section being formed by a top, a continuous wall and floor that form an inverted pie plate shaped interior chamber, wherein a circumference of the top is smaller than a circumference of the bottom; b) an inlet port into the interior chamber through the wall offset from a center axis of the truncated conic section; c) an outlet port at the top of the truncated conic section; d) an open top closed circuit collection channel in the floor; and e) a collection port in the collection channel to thereby create fluid communication from the interior chamber to a sensor array.

In another aspect of the invention the cyclonic separator the collection port can extend through the floor to thereby connect to the sensor array. In yet another aspect of the invention the cyclonic separator the collection port can be formed by a tangential extension of the collector channel, the collector channel extending through the wall to thereby connect to a sensor array. In yet another aspect of the invention the cyclonic separator the outlet can be positioned in a center of the top so that a center axis of the outlet is congruent with the center axis of the truncated conic section and the outlet can be formed by a flow divider with a deflector mound positioned on the floor directly below the outlet. In another aspect of the invention the cyclonic separator the inlet port can be formed by a circular opening at a first end exterior to the interior chamber with a channel from the first opening through the wall of the interior chamber to a second opening where the second opening is elliptical in shape and the channel provides fluid communication from the from first opening to the interior chamber. In yet another aspect of the invention the cyclonic separator a cross sectional area of the channel from the first opening to the second opening can have substantially the same and the channel is on a tangent to a curvature of the wall of the interior chamber. In another aspect of the invention the cyclonic separator is formed as a unity structure of substantially one material with no seams or joints. In yet another aspect of the invention the cyclonic separator it is fabricated by a 3-D manufacturing process to create its single unitary structure.

In yet another aspect of the invention it provides a method for monitoring and analyzing the condition of a fluid flow, which includes the steps of: a) separating particulate matter from a primary fluid flow channel; b) directing objects in the fluid flow to a sensor array so that the objects pass-along a predetermined path; c) interrogating a predetermined field of view along the predetermined path with a plurality of ultrasonic pulses directed along an axis of transmission at an oblique angle to the predetermined path and receiving reflections of ultrasonic pulses from the objects wherein the reflections of ultrasonic pulses are on an axis of reception congruent with the axis of transmission of the ultrasonic pulses; d) generating an inductive field along the predetermined path; e) distinguishing air bubbles from particulate matter among the objects detected based on a received plurality of reflections; f) determining a size of the objects; g) determining if the particle is metallic or non-metallic by combining readings from the ultrasonic reflections and inductive filed readings; and h) determining if a metallic particle is ferrous or non-ferrous from the inductive field readings.

In another aspect of the method of the invention it includes the further step of determining the condition of the fluid. In yet another aspect of the method of the invention the fluid flowing being monitored can be selected from a group of fluids consisting of: beer, wine, milk, ice cream, water, or soda.

In another aspect of the invention it provides a method for training a neural network for identifying failure conditions in a fluid circulation system comprising the steps of: a) monitoring a fluid circulation system with a set of sensors; b) generating a history of raw sensor signals in a time dependent basis of the fluid flowing in the fluid circulating system for a broad range of known good and bad conditions; c) extracting a set of pertinent fluid parameters or features from the sensor signals regarding: i) particles material, size, count and distribution in the fluid circulating in the system; ii) particle distribution change rate; iii) undissolved air in the circulating system; iv) water content; v) fluid temperature; vi) oxidation; d) inputting both the features and known fluid condition into the network (training set) to train a set of weighted connections to handle those particular failure modes.

In an another aspect of the method of training a neural network the step of gathering sensor signals comprises gathering sensor signals form the following sensors: a) an ultrasonic transducer, b) an inductive sensor, c) a fluid quality sensor, and d) a temperature sensor. In yet another aspect of the method of training a neural network the step of monitoring fluid circulation is monitoring a system wherein the fluid flowing in the fluid circulating system is selected from a group of fluids consisting of: oil, beer, wine, milk, ice cream, water, soda, coffee, espresso, chocolate and coco.

The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

FIG. 2A depicts an axial cross-sectional cut-away view of a second embodiment of the sensor cluster of the present invention;

FIG. 2B is a cross-sectional view of the sensor cluster of FIG. 2A along line IIB-IIB;

FIG. 5 is a simple flow chart that summarizes one preferred method the present invention uses to analyze data collected by the various sensors;

DETAILED DESCRIPTION

Figure 1A:
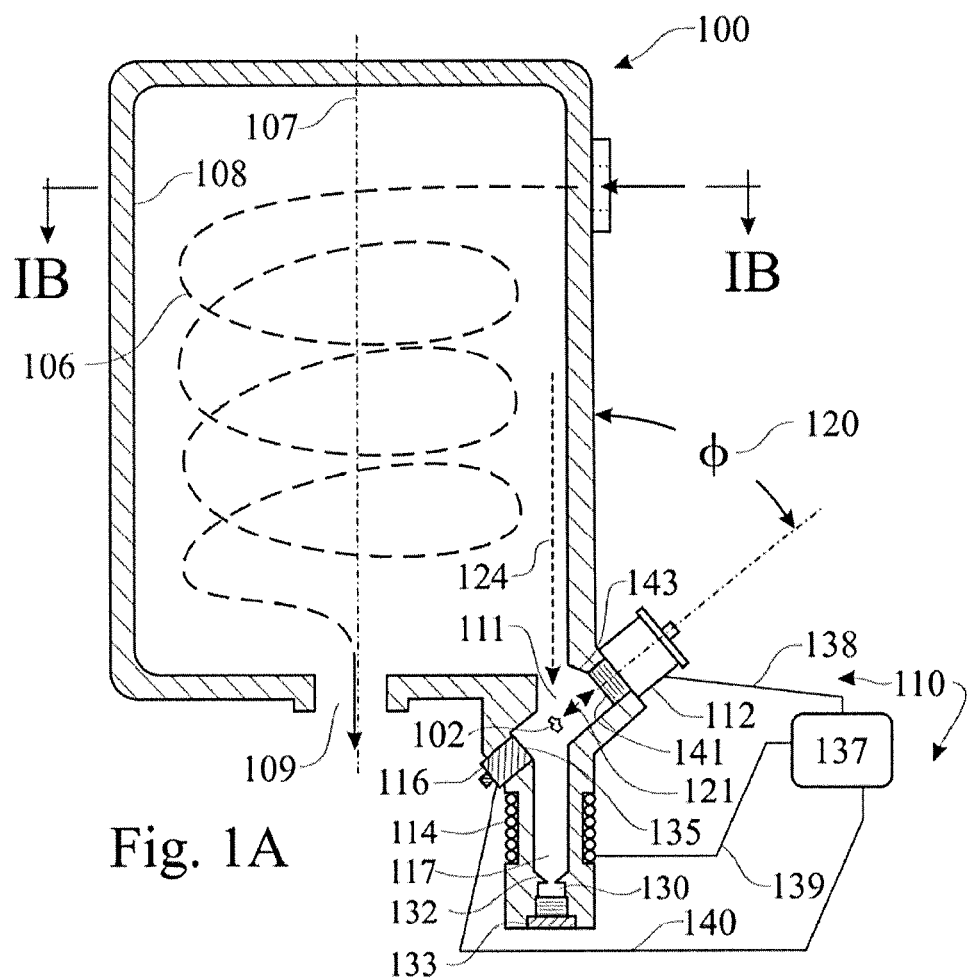
FIG. 1A depicts one variation of the invention which shows an axial cross section of a cyclonic separator with an embodiment of the sensor cluster of the present invention.
Figure 1B:
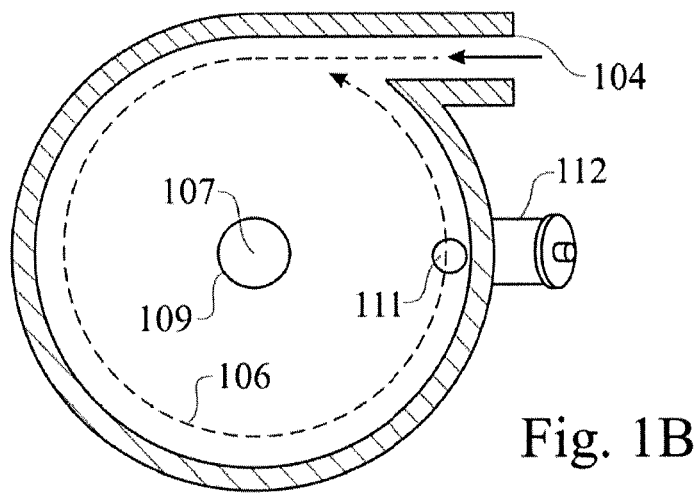
FIG. 1B shows a radial cross-section of cyclonic separator of FIG. 1A along line IB-IB of FIG. 1A.

A First Embodiment of the Sensor Cluster:

FIG. 1A is an axial cross-section of one embodiment of the invention that employs a cyclonic separator 100 with three types of fitted sensors in sensor array 110 for the detection of debris particles in a fluid as well as determine the quality of the fluid itself. A Cyclonic separator 100 is utilized to separate debris particles from a 3 phase fluid flow consisting of fluid, air, and debris particles. The fluid flow enters into inlet port 104 and due to the inlet ports configuration as depicted in FIG. 1B with inlet port 104 offset from the axial center 107 of cyclonic separator 100 induces a strong Cyclonic flow 106. Ultrasonic transducer 112, inductive sensor 114 and oil sensor 116 make up sensor cluster 110.

Referring back to FIG. 1A the cyclonic flow 106 causes all particles above a threshold size to displace radially outward to the Wall 108. Given the characteristics of the fluid and rate of fluid flow, particles as small as 100 microns or less will be urged towards the wall 108 of separator 100. The fluid and air bubbles pass out the outlet port 109 and the separated particles which have been dispersed out towards wall 108 of separator 100 fall by gravity to the base of the separator 100 near watt 108 and eventually fall into sensor cluster 110 through opening 111 where the sensors determine the physical properties of the wear debris particles, as described below. Hence due to gravity the wear debris particles 102 drop through sensor array channel 117 past the sensing zones of ultrasonic sensor 112, inductive sensor 114 and oil quality sensor 116 into a collection trap 130. The collection trap 130 contains and stores all particles separated from the flow and can later be removed and analyzed at servicing intervals. The fluid in sensor array channel 117 is substantially still or stagnant since the sensor array channel dead ends at collection trap 130.

Transducer 112 and sensors 116 and 114 all connect to a computer and power supply 137 by lines 138, 139 and 140 in a standard fashion for control and function. Computer 137 would be programmed in a standard fashion to control operation of sensors 116 and 114 as well as transducer 112 to obtain appropriate data and analyze it.

Ultrasonic transducer 112, which will be described in detail below, is positioned to transmit ultrasonic pulses towards oil quality sensor 116 front surface 135 which front surface presents a flat surface normal to the axis of transmission of transducer 112 for the ultrasonic pulse generated by the transducer to bounce off. Given that the frequency of the ultrasonic pulse generated is known and controlled by the operator and the time it will take the pulse to travel to and from reflection surface 135, if a particle falls into the field of view of ultrasound transducer 112 it will reflect back a portion of the ultrasonic wave before the main portion of the wave is reflected from surface 135 back to transducer 112. Thus, with this first reflection off of the particle or alternatively an air bubble, transducer 112, which is connected to computer 137 will start the process of determining if a particle or air bubble is present. Since transducer 112 generates a series of pulses in a time sequence during the time that the particle or air bubble will be in the field of view of transducer 112 the system can determine if the reflection is from an air bubble or a particle. With each pulse the air bubble will be moving up in the liquid and the particle will be moving down. Because transducer 112 is positioned at an oblique angle Θ 120 with respect to the path of the particle or air bubble, given the downward projection of the axis of transmission 121 of transducer 112 the sound reflection or echo as the result of a subsequent pulse from an air bubble will indicate it is closer since it will be rising in the fluid. On the other hand if second sound reflection or echo indicates the item reflecting the pulse is further away it will indicate it is a particle. This process will be explained in more detail below.

Oil quality sensor 116 is mounted as noted in FIG. 1A in a site near ultrasonic sensor 112 in a manner that is the most compact and simplifies manufacturability. Oil quality sensor 116 monitors various fluid qualities that could be of interest to machinery health maintenance. For example, if the fluid is oil it would monitor water content and oxidation of the oil. In the preferred embodiment of the present invention oil quality sensor 116 uses a capacitive based sensor built into its face 135 to monitor the condition of the oil. However, those skilled in the art will readily see that the present invention can be built with various fluid monitoring sensors to monitor conditions of a large number of different fluid circulating systems. Also, oil quality sensor can be positioned in a different location and a separate target surface would be provided at 135 for transducer 112.

Inductive sensor 114 is a standard type of inductive sensor. It consists of an inductive coil attached to appropriate circuitry, not shown. In standard fashion when a metallic particle falls through the center of inductive sensor 114, the sensor detects its presence and based on the signal generated by the coils the system can determine if it is a ferrous or non-ferrous metallic mass. On the other hand if the particle is nonmetallic inductive sensor 114 will not detect its presence as it falls through the field generated by the inductive coil. However since the inductive sensor 114 is positioned adjacent to transducer 112, in this embodiment downstream from the transducer, the systems computer 137 can be programmed to time stamp the particle detected by transducer 112 and then look for the particle as it passes through the inductive sensors coil and if inductive sensor does not detect the presence of the particle when it should be passing through the field of the inductive sensor it determines the particle is nonmetallic. As an alternative the inductive sensor can be located upstream from the transducer and the system can still function in the same manner to distinguish metallic from non-metallic particles.

Ultrasonic sensor 112 and inductive sensor 114 as noted above are used collectively to detect and identify metallic debris and non-metallic debris. Neither sensor type alone can perform this function. Ultrasonic sensor 112 can detect metallic and non-metallic particles but cannot identify the material type. Ultrasonic sensor 112 can also determine if the particle is in fact an air bubble. Inductive sensor 114 can detect and distinguish between ferrous and non-ferrous metallic particles, but cannot detect non-metallic particles such as ceramic particles.

Thus as noted after a particle falls through the field of view of transducer 112 and it determines it is a particle and not an air bubble it will next fall through the induction field of inductive sensor 114. If the debris particle is metallic, sensor 114 will sense it and based on the signal generated computer 137, which will be programmed to do so, will determine of it is ferrous or non-ferrous based on the signal or non-signal from inductive sensor 114. If the particle is non-metallic computer 137 will determine this fact since the computer will be programmed to expect the particle in the field created by sensor 114 and the fact it cannot detect it will indicate it is non-metallic.

To prevent air bubbles from collecting on the face 141 of transducer 112 beveled edge 143 starts adjacent to face 141 of the transducer and slopes upward thus allowing air bubbles to move upward and away from face 141 and not collect on the face of the transducer. If air bubbles were to collect on the face of transducer 112 it would degrade operation of the transducer to the point it would be ineffective.

Collection Trap 130 has a funnel shaped flange 132 that retains particulate matter 102 that falls into trap 130 if for some reason sensor array 110 is tipped to the side or moved in a reversed gravitational field. Thus, the present invention can be used on aircraft, including fighter aircraft or helicopters as part of the oil circulating system where certain maneuvers of the aircraft, such as steep banking turn or a roll of the craft creates a reserve flow of fluid, in this case oil out of trap 130. Flange 132 helps retain the particles during such maneuvers. Additionally, cap 133 of trap 130 can be magnetized to help retain ferrous metallic particles.

The apparatus is suitable for handling large flow rates without causing unnecessary back-pressure in the oil system line. The close mounting proximity of all three sensors provides an advantage since their access cabling can be routed together and connected to the same electronics package. Transducer angle Ø 120 as defined between ultrasonic sensor Axis 122 and debris path 124 provides a significant performance advantage for ultrasonic sensor 112 for detecting and sizing particles as will be noted below.

A Second Embodiment of the Sensor Cluster:

FIG. 2A is a cross-sectional view cut away of another embodiment 207 of the sensor cluster of the present invention. Opening 111 from the cyclonic separator is at the top. In this embodiment the top portion has a funnel 210. Transducer 212 is aligned along axis 223 with oil quality sensor 216 with transducer 212 transmission face 241 oriented along axis 223. Axis 223 forms an oblique angle θ 220 with center channel axis 221 of sensor cluster 207. Inductive sensor 214 is located at the bottom end of sensor cluster 207 structure.

FIG. 2B is a cross-sectional cut away view along line IIB-IIB which is at 90° to the view depicted in FIG. 2A. Since transducer 212 is oriented and in an upward facing direction along axis 223 and has a flat transmission surface 241 the ultrasonic pulse it generates is reflected off of the face 251 of oil detector 216 back towards transducer 212. The face 251 of oil quality sensor 216 is normal to axis of transmission 223 of transducer 212. Since the ultrasonic wave generated by the pulse is a roughly cylindrical shape as will be discussed below, the wave covers an elliptical area 253 FIG. 2B from point 261 to 263 along central axis 221 of sensor cluster 207, see FIGS. 2A and 2B forms the field of view (FOV) of sensor 212.

Thus debris 102 falling through opening 111 into sensor cluster 207 will be directed by funnel 210 along the central axis 221 of sensor cluster 207 arranged along sensor array channel 217 and be subject to detection by pulses from transducer 212 from point 261 to point 263. The fluid or liquid in sensor array channel 217 which ends in collection trap 230 is substantially still and stagnant.

As noted field of view 253 resembles an ellipse with its major axis aligned with the direction of the target movement (whether up or down). Funnel 210 directs debris particle 102 along central axis 221 such that it remains in the field of view 253 for an extended duration. This enables ultrasonic sensor 212 to interrogate the particle with several pulses of ultrasonic sound to determine its direction and size. Without funnel 210 a particle could fall down along the wall 255 of the passage through the sensor cluster 207. This would result in a shorter dwell time within the field of view 253. The shorter dwell time could result in the particle passing by the ultrasonic sensor 212 without being detected or only being pinged by one pulse. Moreover, the sensing strength is potentially at a maximum and substantially uniform along axis or path 221. An effective angle 220 is about 45 degrees. But as oblique angle 220 can be varied from about 0° to 75° or greater by virtue of design requirements. With angles less than 45° the ellipse becomes more eccentric, thus further extending the effective field of view length and thus increase the number of potential sensing events. With angles larger than 45° the ellipse becomes less eccentric and more circular and in fact the closer it approaches 90° its ability to detect movement diminishes, this aspect will be discusses below in a little more detail. With angles smaller than 45° the logical extreme is to mount sensor 212 at 0° or in the position of plug 235 (without obstacle 232) to provide an unobstructed FOV to the falling wear debris. In this case the targets can be viewed with the maximum potential number of sensing events as they approach the transducer lens. However, in this case particles can collect on face 241 which could be detrimental. Other design features to collect and trap particles would be added by one skilled in the art to keep face 241 flushed of debris buildup. Thus, funnel 210 by directing movement of particles along axis 221 helps enhance the accuracy and effectiveness of the sensor array 207. Directing the particles along or substantially along axis 221 thus results in a uniform or substantially uniform reflected signal which in turn significantly increases the accuracy of the system. However, in the preferred embodiment an angle 220 of about 45° is optimal, but some applications might use different angles depending on the systems use.

Given ultrasonic sensor axis 223 mounting angle, wear debris particle 102 is first detected with first particle echo or reflection as it enters the field of view 253 of the ultrasonic transducer 212, at point 261. As the particle falls through field of view 253 of transducer 212 it will be pinged multiple times sending back an echo or reflected ultrasonic wave. The multiple reflected signals will thus confirm the particles downward movement due to the forces of gravity since the solid particle is denser than the fluid. Given the orientation of the transducer in this embodiment of the invention with each successive (ultrasonic) ping and reflected pulse the particle will appear to get closer to the transducer until it moves out of the field of view of the transducer.

In contrast, as previously noted an air bubble will rise due to its buoyancy. This will be detectable by this embodiment of the invention since the air bubble appearing to move further away from transducer 212 with each successive pulse while the air bubble is within the field of view of transducer 212. Thus, the positioning of the transducer allows it to determine if the item detected is moving up such as an air bubbles or down such as a particle. If Ultrasonic transducer 212 were rather configured with ultrasonic sensor axis perpendicular to the debris path axis no such capability would result. Most of the air bubbles flowing in the fluid within the separator will not enter into sensor array 207. However, a fluctuating pressure environment or due to other causes, air bubbles can precipitate in the fluid in the cavity within the sensor array.

Another advantage of the configuration created by transducer angle Θ 220 is that some debris particles can have a plate-like shape, rather than having a spherical or other shape with a low surface area to volume ratio. Such plate shaped particles can fall through a stagnant fluid with its flat side perpendicular to the movement. The oblique angle of orientation results in the particle presenting a more substantial projected area to the pulse generated by ultrasonic transducer 212 than if the sensor were mounted with ultrasonic sensor axis oriented perpendicular to axis or debris path. The return signal strength of ultrasonic transducer 212 is strongly proportional to an area exposure factor. If ultrasonic transducer 212 were rather configured with Ultrasonic sensor axis perpendicular to the debris path axis no such capability would result.

Ultrasonic transducer 212 in this embodiment is mounted with an upward cant at oblique angle Θ which prevents air bubbles from collecting in the immediate vicinity of the transmission face 241. In contrast, bubbles can rise and stick momentarily to downward canting surfaces such as face of oil quality sensor 251. The air bubbles will rise naturally away from an upwards canting surface such as 241, than if it were canted downwards as described in the previous embodiment. The presence of an excess quantity of gas bubbles can attenuate or completely block the signal of ultrasonic transducers. Moreover, the upwards canted configuration of all interior surfaces in the sensor array thus enable bubbles to rise upward and eventually purge through funnel 210.

Oil quality sensor 216 is not inordinately affected by bubbles. The sensor needs only to be exposed to the fluid and be in close proximity to the main flow such that the fluid characteristics that it monitors diffuse quickly to it. The downward canting orientation guarantees that no debris can be trapped within it. Oil quality sensor 216 is made with a smooth planar face 251 that faces transmission face 241 of ultrasonic transducer 212. Face 251 of sensor 216 provides surface for a special return signal that defines the acoustic space between it and transmission face 241 of transducer 212 and provides a calibration marker for the system. The calibration marker defines the acoustic space, enables the system to perform a preliminary diagnosis, and aids in particle size estimation. Ultrasonic transducer 212 is mounted with a suitable mechanical method such as threading its outer case into mounting boss and sealing with a polymer seal according to conventional methods. Likewise, Oil quality sensor 216 attaches to a mounting boss and can be sealed in a similar manner.

Debris particle 102 also falls through magnetic field of spiral inductive coil 214. Coil can be powered through voltage plus, and voltage minus. If a metallic particle enters the field, a measurable inductance change occurs and can be calibrated to particle size and whether it is ferrous or non-ferrous.

Although FIGS. 2A and 2B do not include computer 137 and connecting lines 138, 139 and 140, their exclusion is only to provide an uncluttered view of the embodiment depicted in both drawings. In operation the system shown in FIGS. 2A and 2B would include a computer and connections via lines or wireless system when installed.

Figure 3A:
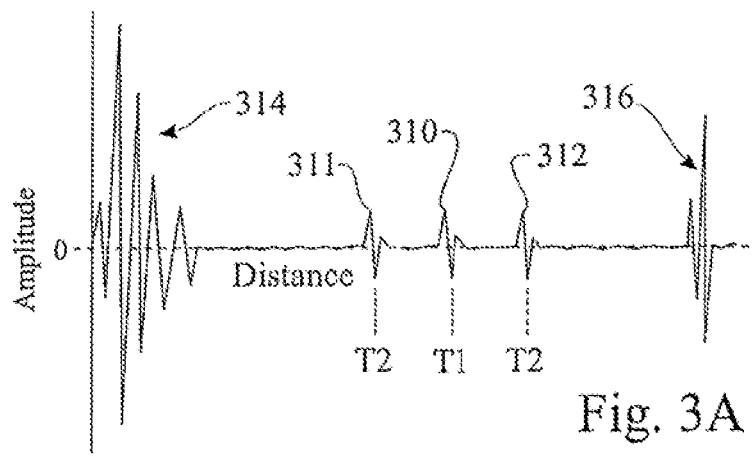
FIG. 3A is a graph of an ultrasonic sensor pulse echo receiver response showing the pulse echo shift for particles or bubbles of air detected.
Figure 3B:
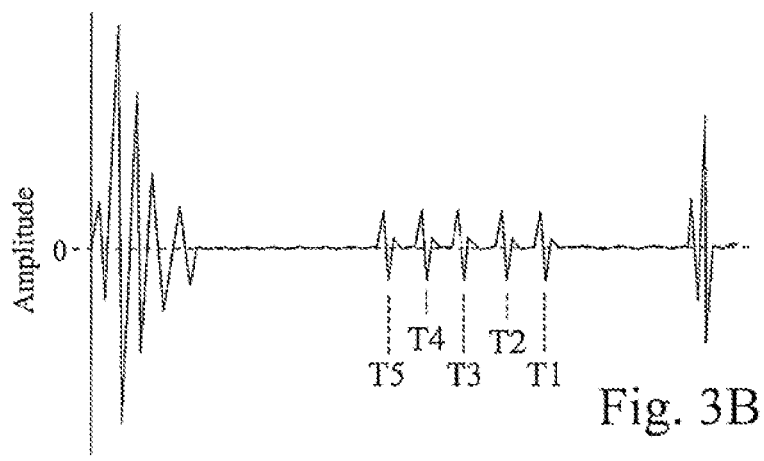
FIG. 3B is a graph of a series ultrasonic pulse echo's reflected off of the same particle as it moves through the field of view of the sensor.
Figure 3C:
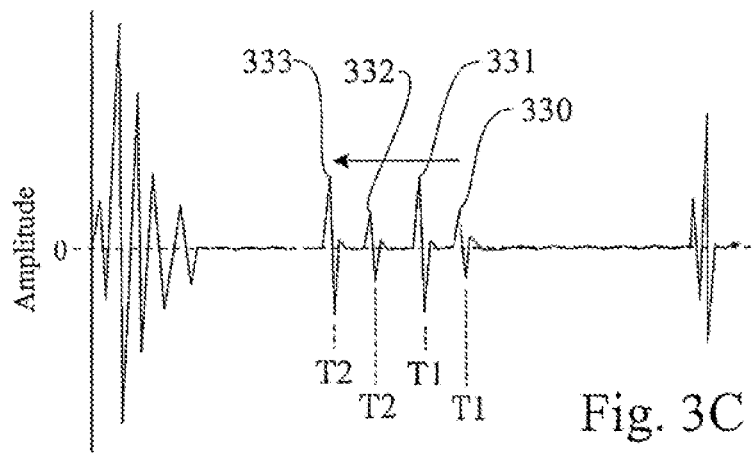
FIG. 3C is a graph of pulse echo's reflected off of particles of two different sizes at two different times as the particles move through the field of view of the sensor.

Detection:

FIGS. 3A, 3B and 3C provide a graphical representation of the various reflected signals that the transducers 112 and 212 receive in response to Ultrasonic interrogation pulses with reflections or echoes from targets in the acoustic field of view. The y-axis represents the amplitude of the wave and the x-axis represents the distance the object reflecting the wave is from the transducer with the transducer being located at zero on the x-axis and y-axis.

Referring to FIG. 3A, 314 is ring down acoustic behavior internal to the transducer, of reverberations, or ring down, from the interrogation pulse generated by transducer 112 or 212. 316 is the reflection of the interrogation pulse off of the face of oil quality sensor 116 or 216 respectively. 310 is the first echo received when a particle or air bubble enters the field of view of the transducer at time $T_1$ which is a reflection of the interrogation pulse generated by the transducer. 311 and 312 are subsequent echoes reflected by a particle from a subsequent or second pulse generated by the transducer at a subsequent time $T_2$. As noted above transducers 112 and 212 generate periodic pulses at preset intervals. These intervals can typically be 3 milliseconds apart; however the pulse intervals can be varied depending on the application and need.

Transducer 112, given its position and the angle of its axis, the subsequent echo or reflected pulse 311 received at time $T_2$ being closer to transducer 112 would indicate that the object is rising and thus an air bubble. On the other hand if at time $T_2$ reflected pulse 312 appears, this indicates the item has moved further away from transducer 112 thus indicating it is a particle moving down through the fluid.

With respect to transducer 212, given its position the opposite would be the case. After a first pulse at time $T_1$ with the item generating a reflected signal at 310, if at time $T_2$ the second reflected signal is at 311 it would indicate that it is a particle failing down through the fluid since second signal 311 indicates it is closer to transducer 212 than the first pulse 310 received at time $T_1$. On the other hand if the reflected signal indicates the item reflecting is at 312 it would indicate the item is moving away from transducer 212 and thus is an air bubble rising in the fluid.

Whether a Debris particle 102 or an air bubble is in the field of view of one of the transducers or not, the interrogation pulse propagates until it hits the face of the oil quality sensor and generates back wall reflected wave 316. Back wall wave signal 316 is used to determine the strength of the interrogation pulse and proximity of targets for calibration purposes. The physical distance from the origin to 316 in the preferred embodiment corresponds to ½ of the elapsed time. A factor of ½ is imposed since the acoustic wave propagates from transducer face 241 to the back wall 251 then returns all of the way back. This is two lengths traveled between 241 and 251. This distance can be calculated from the speed of sound in the fluid.

One of the considerations that the current invention deals with is the ring down phase of the initial ultrasonic pulse 314 generated by the Ultrasonic transducer. A portion of the initial pulse as noted above reverberates within the transducer and if not dealt with by appropriate means can mask the detection of the reflected signal. The current invention deals with this problem by designing the transducer so that it dampens down the ring down of the initial generated pulse. The solution to this problem will be discussed below with respect to various preferred embodiments of the transducer of the present invention. As according to the art for general use of Ultrasonic transducers, the ring down time zone effectively blocks the practical use of sensing within close proximity to the front face such as 241. However, for the embodiments described above, transducers 112 and 212 are set back by an appropriate degree from the target zone which surrounds and is in close proximity to the intersection of axis 221 and 223. The side of the target zone, or a path that a particle can fall, that is closest to the transducer is set to coincide to just beyond ring down zone 314. The transducer is set back no further than this as to maximize the natural echo signal strength, since the strength diminishes as a function of distance due to attenuation caused by the fluid. In the embodiment of the invention disclosed the distance from the intersection of axis 221 and 223 needs to be about ½" to ⅝". However, those skilled in the art will appreciate the actual distance can vary depending on the system, it size fluid, etc. Moreover, the transducer as applied to the methods of this invention does not have to be as highly damped as is the case with conventional ultrasonic transducers. The primary advantage to this is that a more sensitive transducer can be designed and used. That is, there is a natural tradeoff between dampening and sensitivity.

FIG. 3B depicts a series of echoes or reflected ultrasonic waves transducer 212 might receive from the periodic ultrasonic pulses it generates. At T1 it receives the first echo from a particle falling through its field of view and at successive times T2, T3, T4 and T5, it receives successive echoes from the same particle as it falls through its field of view. FIG. 3C depicts another variation where transducer 212 detects two particles of different size falling through its field of view. At time T1 transducer 212 receives two echoes 330 and 331 and at subsequent time T2 it receives two pulse additional echoes 332 and 333 while the two particles are in its field of view. Echoes 330 and 332 would be reflected from the same particle. Likewise echoes 331 and 333 would be reflected from another distinct particle. Since the amplitude of the echoes 331 and 333 are larger than the echoes 330 and 332 it would indicate the particle reflecting echoes 331 and 333 is larger than the particle that reflects echoes 330 and 332. Also, multiple targets of even the same size can appear within the transducers FOV during a single interrogation pulse and represented by multiple return pulses visible in a single return waveform. Thus it can be discerned whether there are multiple targets in the field of view, regardless of size. The same logic can be applied to bubbles and mixtures of bubbles and particles, as introduced above. Particle size is determined from the total energy of the return pulse, calculated from the peak signal amplitude and the pulse-width of the return pulse. Integration of this pulse, plus other salient waveform features, provide an accurate measurement of particle size. Also, averaging several results from multiple interrogation of the same particle, as it drops through the transducer FOV, improves the particle sizing result.

Figure 4A:
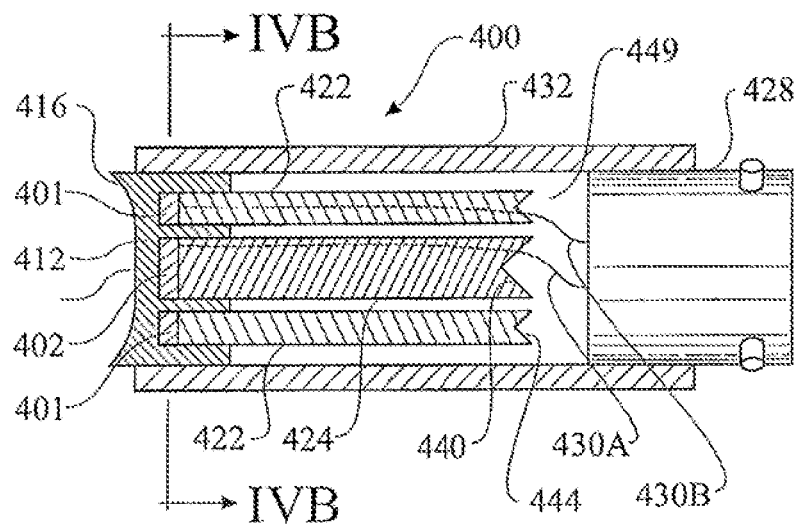
FIG. 4A is a cross-sectional cut-away view of an ultrasonic transducer of the present invention along its axial view.
Figure 4B:
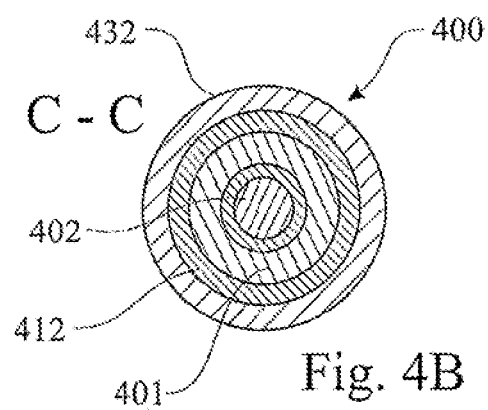
FIG. 4B is a cross-sectional view along lines C-C of FIG. 4A.

The Transducer:

FIG. 4A is a cross-sectional interior view of one of the preferred embodiments of a transducer 400 of the present invention. The transducer 400 is cylindrical in shape and FIG. 4B is a cross-sectional view along C-C of FIG. 4A in the direction indicated by the direction of the arrows on line C-C.

Referring back to FIG. 4A transducer 400 has a first crystal transceiver 401 which is shaped as a ring and a second crystal transceiver 402 that is shaped as a disk surrounded by an encasing cylindrical tube 432. Covering the front of crystal 401 and 402 is acoustic lens 412 which has a flat front surface 416. Acoustic lens 412 attaches at its edge to encasing tube 432 and has pockets 405 and 407 into which crystals 401 and 402 fit. Dampening element 424 which has a cylindrical geometric shape attaches to the back of crystal 402. Dampening element 422, which also has a tubular geometric shape attaches to the back of crystal 401. Connector 428 is positioned at the back of transducer 400 and connects by low gauge cable 430A and 430B to transceiver crystal 402 and 401 respectively.

Transceiver crystals 401 and 402 in the preferred embodiment are piezoelectric ceramic material (PZT), lead zirconium titanate. The preferred embodiment depicted in FIGS. 4A and 4B because of the flat front surface 416 of acoustic lens 412 creates a flat circular collimated sound wave on activation of one or both of the transducer crystals 401 and 402. In the preferred embodiment the biostatic configuration of the crystals 401 and 402 calls for one of the transceivers to transmit an ultrasonic pulse and the other transceiver to receive the reflected or echo ultrasonic pulse. Since both transceiver crystals 401 and 402 reside in the same lens assembly 412 and thus are aligned along the same transducer central axis (223 FIG. 2A and 121 FIG. 1A) they are naturally aligned to the same field of view 253 as depicted in FIGS. 2A and 2B. Thus one of the PZT elements 401 or 402 can be used to transmit ultrasonic pulses and one can be used to receive the reflected ultrasonic echo or reflection from particle in the transducers field of view or the planar face 251 of oil quality sensor 216.

As noted first PZT crystal 401 is shaped as a ring, and a second PZT crystal 402 is a disk are set into pockets within acoustic lens 412. Lens 412 is most preferably constructed of peek or ULTEM plastic, due to the materials high heat resistance, hardness and toughness. Alternatively, the lens 412 can be molded from an appropriate high temperature resisting epoxy material, and potted with accompanying parts in a single layup. Acoustic lens 412 in a preferred embodiment has a planar face 416, in certain applications it can have a concave face. The planar face 416 generates a cylindrical or collimated focal zone to monitor a larger sample volume; whereas the concave lens face generates a converged focus as the general concept is commonly understood in the art. More specifically, in contrast to prior art or other methods, the purpose of this embodiment is to not fully focus the acoustic interrogation pulse to an infinitesimally small volume, but to strategically concentrate acoustic energy within the target zone which is a finite and substantial volume. Thus, for example, the portion of lens 416 over element 401 when used as the interrogation function can assume an optimal combination of spherical, conical, or parabolic geometry that is known in the art to concentrate acoustic waves at a distance from the transducer face. Also, the region of lens 416 over element 402 when used as the receiver can remain flat, to provide optimal sensitivity to return echoes. As a further refinement one may employ a partially focused concave lens embodiment, since the acoustic gradient of focus intensity will naturally increase towards the back of the target volume. This will compensate for the tendency for the return echo from a potential target that naturally attenuates with distance. Thus, an optimized partially-focused interrogation can compensate for this distance to provide more uniform return signal amplitude throughout the target zone. This method eliminates a time variable that otherwise must be compensated for by the particle sizing algorithm.

Dampening element 422 is fitted to the inboard side of a first PZT Crystal 401 and dampening element 424 is fitted to the inboard side of second PZT Crystal 402. The dampening elements attenuate the crystal ring down signal 314 of the interrogation pulses; the PZT crystal(s) can otherwise exhibit an extended vibration period and generate acoustic noise such that the received acoustic signal is corrupted. Dampening element 422 is configured as a tube; dampening element 424 is configured as a cylinder. Appropriate materials for the dampening elements are known in the art as typically consisting of mixtures of an epoxy matrix and granules of a dense material such as tungsten. The granules augment the dampening process since they absorb, deflect and scatter acoustic waves. The distal end of each dampening element is shaped to further provide a dampening effect. Damping element 424 has a v-notched profile groove 440. The damping element 422 also has a V-notched groove 444. In the preferred embodiment the geometry of each of the groves 440 and 444 is an acute angle under 45 degrees between the sides of the groves. This feature radially deflects the axially propagating residual acoustic interrogation wave to limit its reflection back to the PZT crystal element. The dampening elements are configured to not directly contact one another, which prevents signal cross-contamination. As noted PZT crystals 401 and 402 are electrically connected to connector 428 with a low-gauge cables 430A and 430B with techniques common to the art. The cables can be routed through void 449. Acoustic lens 412, PZT crystals 401 and 402, and dampening elements 440 and 444 are bonded together with an appropriate high temperature resisting epoxy. The epoxy also pots and encapsulates the crystal-side terminal ends of cables. Acoustic lens 412 is bonded into tube 432. Connector 428 can be bonded into, screwed into, or constrained with a set screw to tube 432. As an alternative the void or open space 449 at the back of transducer 400 and between dampening elements 424 and 444 and casing 432 can also be filled with additional dampening materials such as a high viscosity fluid.

Figure 4C:
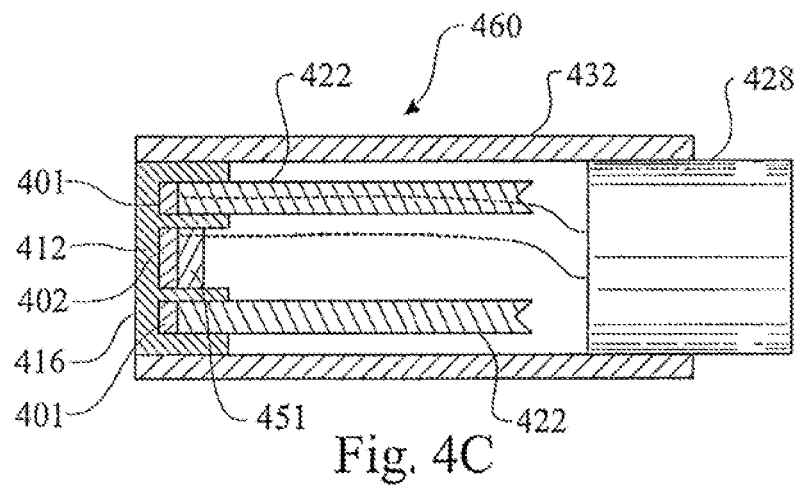
FIG. 4C is a cross-sectional cut-away view of another embodiment of an ultrasonic transducer of the present invention.
Figure 4D:
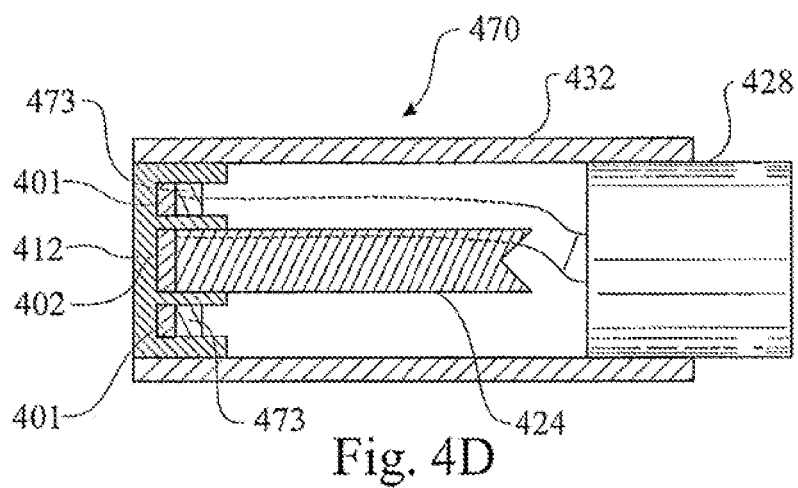
FIG. 4D is a cross-sectional cut-away view of another embodiment of an ultrasonic transducer of the present invention.

FIG. 4C provide a cross-sectional view of an alternative preferred embodiment 460. In this variation all the elements are the same as those on embodiment 400 depicted in FIGS. 4A and 4B with one exception. Dampening element 451 attached to the inboard side of PZT crystal 402 is a relatively thin disk in contrast to a cylinder or rod 422 of crystal 401. Thin disk 451 increase the sensitivity of crystal 402 for reception of reflected or echo waves. In this variation of the transducer 460 PZT crystal 401 generates interrogation pulses and PZT crystal 402 receives the echo or reflected Ultrasonic waves. The small dampening element 451 increases the sensitivity of crystal 402 by not over dampening the echo or reflected return signal. FIG. 4D provides a cross sectional view of another embodiment of the transducer of the present invention 470. In this variation all of the elements are the same as those in the embodiment 400 and numbered the same except dampening element 471 is attached to transducer crystal 401. The small dampening element 471 attached to transducer 401 increases the sensitivity of transducer crystal 401 to incoming echoes or reflected ultrasonic waves. Thus, in this embodiment crystal 402 transmits the ultrasonic pulses and crystal 401 is the receiver, and receives the reflected echo.

Figure 4E:
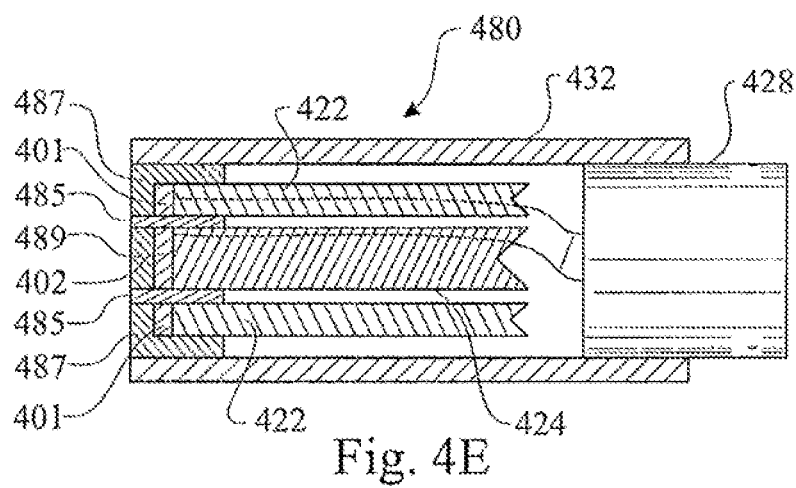
FIG. 4E is a cross-sectional cut-away view of another embodiment of an ultrasonic transducer of the present invention without a transducer lens.
Figure 4F:
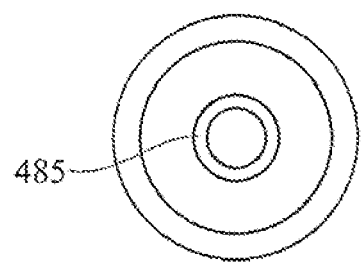
FIG. 4F is a view of the end of the embodiment of the ultrasonic transducer depicted in FIG. 4E without a transducer lens.

FIGS. 4E and 4F illustrate yet another embodiment of the transducer. In this variation all of the elements are the same as those depicted in FIGS. 4A and 4B and numbered the same with the exception that transducer lens 412 has been eliminated and only an isolating acoustic insulating ring 485 is positioned between crystals 401 and 402 to acoustically isolate them. In contrast, the embodiments of 4A, 4B, 4C, and 4D all utilize a shared lens 412, 416. However, this results in a degree of acoustic contamination of the receiver portion. This will require a longer ring down time to provide an acoustically clean reception field, and hence the transducer will need to be placed further from the target zone. On the other hand this embodiment can share the return echo since even if the echo impinges with the transmit portion of lens 416, some return signal is obtained. There is a tradeoff in the effect between versions 4E, 4F and versions 4A, 4B, 4C, and 4D. The latter can be placed closer, get a stronger return echo but miss part of it.

A Method for Implementation:

A Method to implement the invention is illustrated in FIG. 5 is a simple flow chart that summarizes one preferred method the system uses to analyze and organize the data collected by the sensors described above. These routines consist of ultrasonic debris sensing routine 501, inductive sensing routine 503 and oil quality sensing routine 505.

Regarding routine 501 at step 511 the ultrasonic sensing routine as conducted by the Acoustic Debris Monitor (ADM) (the proposed trade name for the ultrasonic transducer of the present invention) periodically transmits a signal at an oblique angle towards path along which the debris particles are moving. Reflected echoes from particles or air bubbles are received the by transducer described above. Computer 157 operating with appropriately software based on the readings received determines if the particle moving through its field of view is a solid particle or an air bubble it determines the size of the particle and collects the information on size and count for tabulation 512. The routine also time stamps each particle and sends 515 this information to inductive routine 521. At step 517 the system can include the step of comparing the count calculations and size of the particles to a stored minimum count and threshold size. If the particle count or particle size reaches a threshold count and size the system can signal an alarm condition.

Inductive sensor routine 503 upon receiving the time stamped information from the ultrasonic debris sensing routine 501, determines, based on the flow characteristics of the fluid, when the time stamped particle should be moving through the field created by the inductive sensor. If it cannot detect the particle it determines it is non-metallic 523. If the particle is metallic, the inductive sensor detects its presence and determines if it is ferrous or non-ferrous 524. At step 529 based on the time stamp of the event identifying each particle the information is collected and collated as non-metallic, metallic non-ferrous, or ferrous particles. The information is also tabulated at step 529 with the information obtained by routine 501.

Additionally, running in parallel is fluid quality sensor routine 505, which based on the conductivity and polarity readings is assessing the moisture content and oxidation of the fluid or other aspects of the fluid depending on the fluid system being monitored 527. The routine programmed at step 527 could include in an oil lubrication system an alert if the water content of the oil exceed a certain threshold such as 50%. Depending on the system if water reaches a certain threshold percentage it will start to come out of solution and corrode the bearings or other metal parts of the system. The information from the fluid quality routine is collected and tabulated with the other information 529. All of this information then provides critical information regarding the condition of the fluid in the system under observation. In the preferred embodiment of the sensor at 505 is a polymer bead matrix sensor.

Although the description of the invention herein uses the example of an oil lubrication system in describing the invention at various points in this disclosure, the system can be used for the monitoring of the condition of a wide variety of fluid circulating systems or liquid stream systems. Not to limit the applicability of the invention as described herein it could be used in a soft drink production plant, a brewery, milk processing system, ice cream production plant, a public drinking water system or any other of a number of systems or plants that need to monitor the quality and condition of a liquid flow or liquid stream. For example the system of the present invention could be used for measuring the $CO_2$ bubble size and amount in a brewery or soda processing plant. A bleeder tube or exit port could be added to the bottom of the sensor array and the flow of the fluid through the sensor array circulated back to the main flow to count air or $CO_2$ bubbles and determine size. The concept of passing the fluid through the sensor array and then recirculating the fluid back to the main flow of fluid could be uses with other fluid flows.

A Method for Creating Fusion-Neural Network Monitoring System

Wear debris (acoustic and inductive) and water content signals are merged by data fusion technology to learn and classify failure modes of the lubrication machinery such as a gearbox. Data fusion is used to improve the performance of the diagnosis capability. It can also perform inferences that are not possible from a single sensor alone. Because of the diversity of failure type, several kinds of quantities are used that are effective for identifying different failures. Measurements taken using single sources are not fully reliable and are often incomplete due to the operating range and limitations that characterize each sensor. In addition, sensor signals can be corrupted by noise or can malfunction all together. Fusing their measurements can provide a more robust and reliable reading than that from any one sensor since signals tend to be correlated between sensors whereas noise is uncorrelated.

Fusion methods include Neural Networks such as the Radial Basis Function Network and Backpropagation Network. The advantage of using neural networks is that they can handle non-linear correlations involving sudden transitions or complicated interactions among input variables. They are also robust to sensor noise and malfunctions. The neural network is trained by first inputting known fluid measurements (training set) for a range of known good and bad conditions and training the network to recognize these cases. The training set consists of a set of sensor features. The features are generated by processing the individual raw sensor signals and extracting pertinent data about the state of the fluid. The features include particle counts, particle size, particle material, particle distribution changing rate, water content, oil temperature, etc. Once the network is trained it can be applied to a new set of fluid measurements and provide a means of analyzing data and relating the new measurements to learned failure modes of the machinery.

Figure 6:
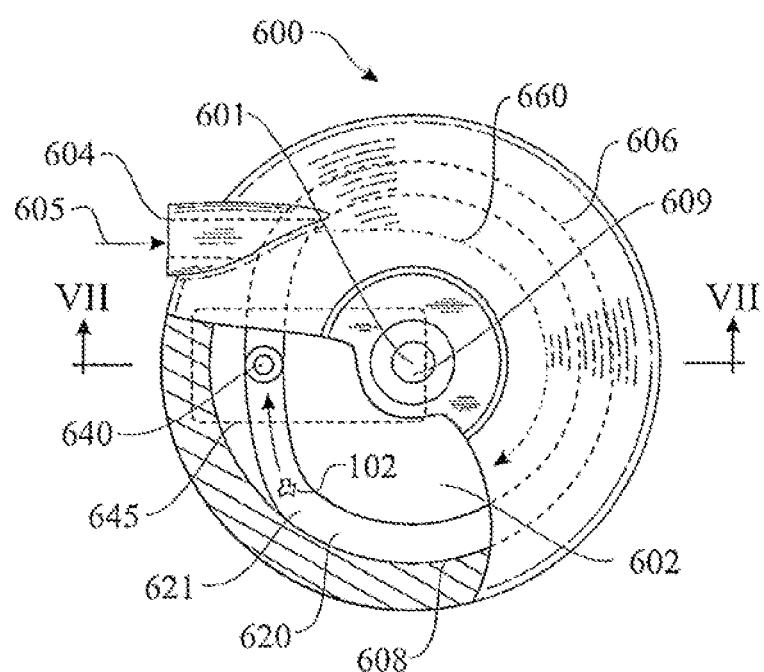
FIG. 6 provides a top view of a preferred embodiment of a cyclonic separator of the present invention with a partial cut-away view of the interior.
Figure 7:
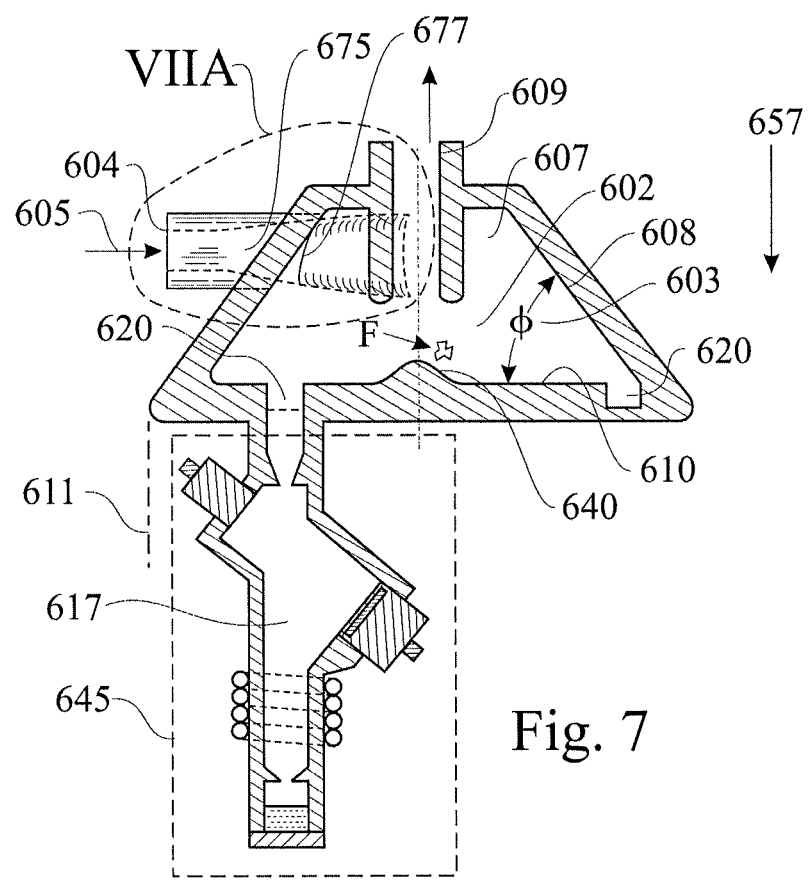
FIG. 7 an axial cross-sectional view of the cyclonic separator of FIG. 6 along line VII-VII.

A Preferred Embodiment of the Cyclonic Separator:

FIG. 6 provides a top view of a preferred embodiment of a cyclonic separator 600 according to the present invention; with the top partially cut away to provide a partial view of the interior. FIG. 7 is a cut-away side view of separator 600 along line VII-VII on FIG. 6 in the direction of the arrows.

Referring to FIG. 7 inlet port 604 is at an offset position from the center axis 601 of separator 600 and located near the top 607 of the interior. Outlet port 609 is located at the top center of the separator. Referring to FIG. 6 and FIG. 7 collection channel 620 is located in the floor 610 of the separator 600 and makes a complete circuit around the floor 610 adjacent to the inner wall 608 with the exception of diversion turn 621 where channel 620 diverges from wall 608 and connects to collection port 642 which leads into the sensor array channel 617, the position of which is under the separator and indicated by the outline 645. Since sensory array channel 617 ends in a dead-end the fluid in sensory array channel 617 is substantially still or stagnant.

Referring again to FIG. 7 the positions of inlet port 604 and outlet port 609 can be seen. Outlet port 609 is coextensive with flow divider 630. The inner wall 608 makes an acute angle 603 with the floor 610 of separator 600. A portion of collection channel 620 can be seen on the right side adjacent to the wall 608 and in the diversion turn 621 area on the left where it meets collection port 642 which creates an opening into the sensor array 207. Additionally, cyclonic separator 600 in FIG. 7 is in the position it would normally be operating with the gravitational field being downwards as depicted by arrow 657.

As can be seen from FIGS. 6 and 7 the shape of the interior 602 of cyclonic separator 600 is a truncated conic section, where the top 607 is circular in shape and has a smaller diameter than floor 610 which also has a circular shape. Top 607 and floor or bottom 610 are connected by continuous wall 608. Thus, the ideal interior shape is a conic section cut by two parallel planes, which intersect at right angles the central axis of the conic section. This creates the truncated conic section which looks like an inverted pie dish or pan.

Referring to FIG. 6 fluid entering cyclonic separator at inlet 604 in the direction of arrow 605 hits interior wall 608 and is diverted in a circular path 660. As more fluid enters it continues in a circular flow and is forced downwards into the interior of chamber 602. Particulate matter 102 is forced out to the edge of the chamber and eventually falls into collection channel 620. The particulate matter 102 then is moved along collection channel 620 where it eventually falls through drop port 642 into the sensor array 207 where its composition and size is determined by the sensor array 207 as described above in detail. The fluid circulation in cyclonic separator 600 is eventually forced out through outlet 609. Given the higher pressure in the fluid along the wall air bubbles in the fluid will also tend to be forced to the center and out through outlet 609. Deflection mound 640 prevents particulate debris 102 from collecting in the bottom center of separator 600. Diversion turn 621 of collection channel 620 allows for the placement of sensor array directly under cyclonic separator 600 and thus prevents it from protruding beyond the profile of the separator bounded by dashed line 611. The system of the present invention, including the cyclonic separator 600 can be used in a wide variety of systems to analyze and determine the condition of fluid flowing in a system. This can vary from fluid flow systems of soda plants and breweries to the oil circulating systems of helicopters and fighter jets. The ability to provide a compact package of the system is often an important feature.

Figure 7A:
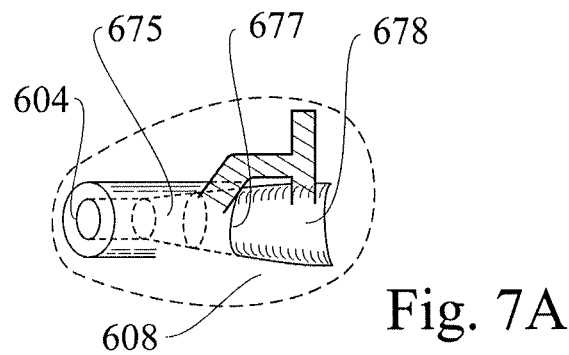
FIG. 7A is a sectional view VIIA of FIG. 7.

Referring to FIGS. 7 and 7A inlet flow channel 675 indicated in outline form progresses in smooth transition from a circular inlet port 604 to an elliptical opening 677 into the interior chamber 602 near the top of interior 607 of separator 600. Thus channel 675 progresses from a round channel to an elliptically shaped channel where in the preferred embodiment the cross sectional area of the channel remains roughly the same from the round inlet to the elliptical outlet. Inlet channel 675 enters at a tangent to the curve of the interior wall 608 so an open portion 678 of inlet channel 675 continues in the wall 608 to complete the open extension of the channel 675 in wall 608. The shape of inlet channel 675 as described results in fluid flowing in channel 675 entering in a smooth laminar flow and avoiding a turbulent chopping flow of fluid into interior 602. Acute angle 603 forces fluid in top of interior 607 downwards and radially outwards away from the outlet to prevent the turbulent mixing of the particle laden inlet flow with the clean outlet flow. The geometry is so effective that flow divider 630 in some instances may not be necessary.

Figure 8:
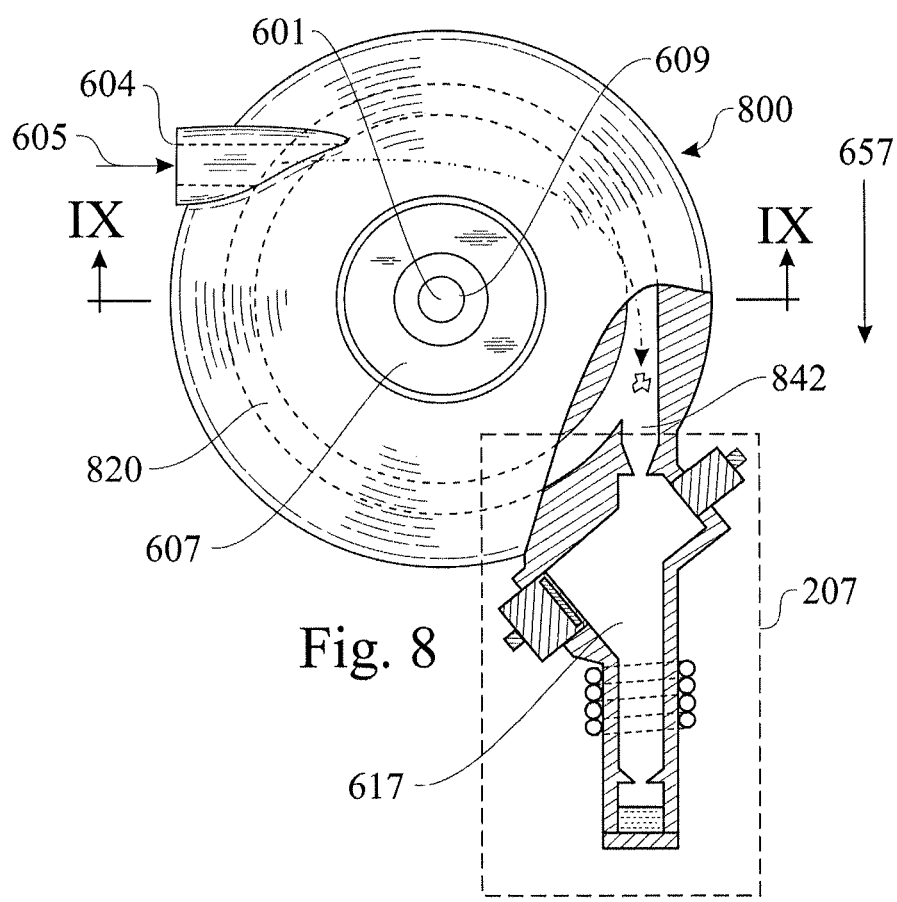
FIG. 8 provides a top view of another variation of a preferred embodiment of the cyclonic separator of the present invention with a partial cut-away view of the interior and attached sensor array.
Figure 9:
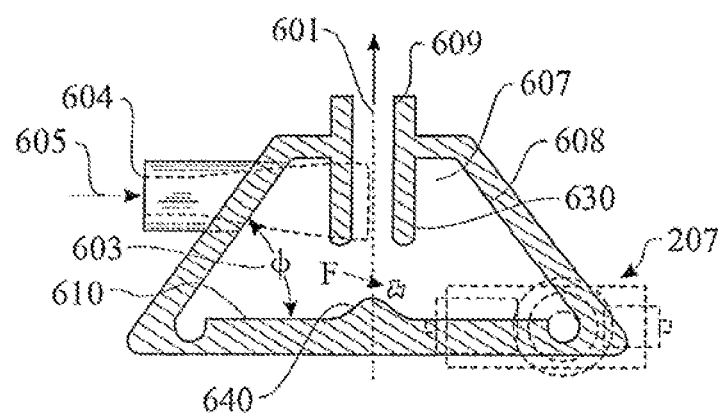
FIG. 9 is cross-sectional axial view along line IX-IX of FIG. 8.

Another Variation of the Cyclonic Separator:

FIGS. 8 and 9 provide another variation of the cyclonic separator of the present invention. The variation of the cyclonic separator 800 in FIG. 8 is similar in some respects at that depicted in FIGS. 6 and 7. Accordingly, when the feature of separator 800 is the same as separator 600 the same reference number will be used. When it is different a different reference number will be used.

Referring to FIG. 8 cyclonic separator 800 is depicted in its upright position, in the orientation it would have when it is in use. The gravitational field 657 being in the down direction. Inlet port 604 and outlet port 609 are visible. Additionally, from the cut-away view on the lower right side, a portion of collection channel 820 can be seen with the rest of channel 820 appearing in outline form. Sensor array 207 attaches to tangential extension 842 of collector channel 820. Thus tangential extension 842 acts as a collector port. As noted above acute angle 603 forces fluid in top of interior 607 downwards and radially outwards away from the outlet to prevent the turbulent mixing of the particle laden inlet flow with the clean outlet flow. The geometry is so effective that flow divider 630 in some instances may not be necessary.

FIG. 9 is a cross-sectional view of separator 800 in FIG. 8 along line IX-IX in the direction of the arrows. Inlet port 604 and outlet port 609 can be seen. Top of interior 607 connects to continuous wall 608. Continuous wall 608 connects to bottom 610 to form the truncated conic section (the same shape as in the previous embodiment) which has the shape of an inverted pie plate or pan. In this variation collection channel 820 circumscribes the entire edge of floor 610 where it meets wall 608. Deflection mound 640 is in the center. In FIG. 9 the position of sensor array 207 is shown in outline to indicate its position on in the side profile view shown in FIG. 9.

The embodiment of the invention depicted in FIGS. 8 and 9 functions in a similar fashion as that depicted in FIGS. 6 and 7. Referring to FIG. 8, the fluid enters cyclonic separator through inlet 604. It then flows in a circular clockwise flow around axis 601 of separator 800. Given the truncated conic shape the flow is forced down along wall 608 toward floor 610 and then when it passes below the inside bottom edge of flow divider 630 is forced out through outlet 609. Particulate matter 102 is forced down into collector channel 820 and then out collector port 842 into sensor array 207. In this embodiment, in contrast to the embodiment of FIGS. 6 & 7, by virtue of the flow geometry, the particles are swept directly into collection port 842.

The discussion of sensor array 207 above describes what happens once particulate matter 102 is directed into sensor array 207.

A 3-D printing process is particularly applicable for the manufacture of embodiments 600 and 800 of the cyclonic separator. 3-D printing is available in polymer and metal materials. The latter is available in aerospace-appropriate materials such as Titanium, Aluminum, and Stainless Steel. A 3-D printed version can achieve a seamless construction. Such a construction would simplify the construction and lower the unit's bulk and weight by eliminating a seam, a seal, and fasteners. Moreover, in regard to conventional molding processes, the elliptical-transitioned inlet depicted in FIG. 7A could prove to be infeasible to mold while using conventional methods. 3-D printing, as opposed to conventional molding, allows undercuts and do not require draft angles that are otherwise needed to eject the part from the mold. A seamless unit eliminates leak-prone seams and thus represents a more reliable approach. A seamless unit would thus most likely be a single unitary structure wherein all of the surfaces and ports are built into one structure with no seams of separate parts. Both of the preferred embodiments described above and depicted in FIGS. 6, 7, 7A, 8 and 9 can be manufactured by a 3-D manufacturing method to achieve the desired shape.

Figure 10:
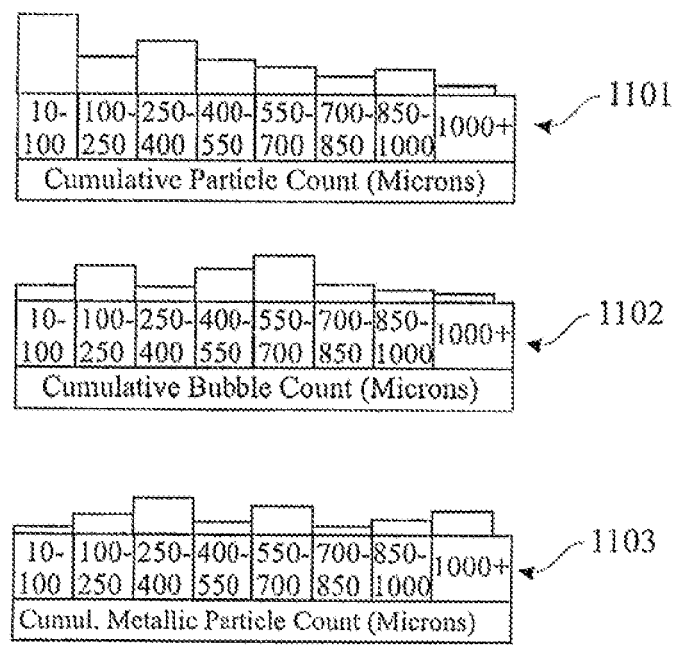
FIG. 10 is sensor output histogram of information generated by the system and apparatus of the present invention.

Tabulation of Information:

FIG. 10 provides a sensor output histograms of information generated by the apparatus and system of the present invention. Three different histograms are shown, for cumulative particle count 1001, cumulative bubble count 1003 and cumulative metallic particles count 1005.

Each histogram has different size categories of particles presented along the x-axis and the particle count is shown on the y-axis. The higher the column on the y-axis the more particles or bubbles of the particular size category, which ranges from 50 microns to 1000+ microns. The first category being 50 to 100 microns. The second 100 to 250 microns, etc. The size ranges can be adapted to the particular application.

Figure 11:
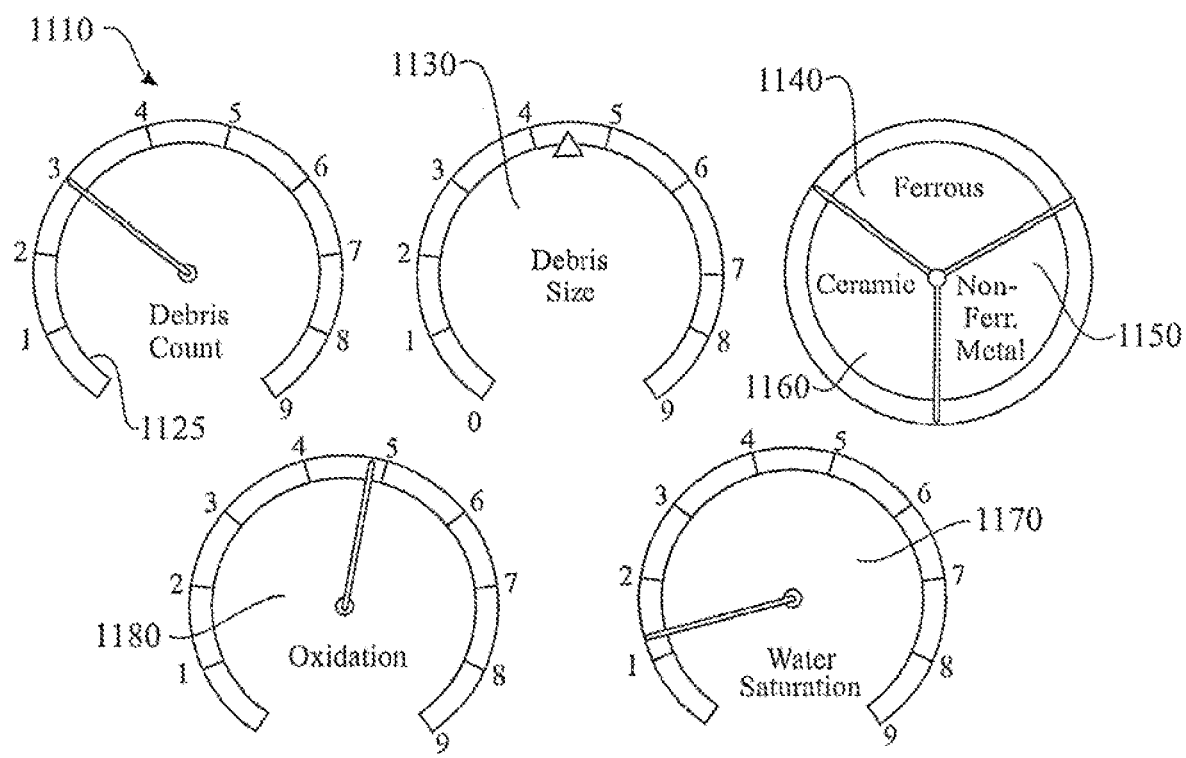
FIG. 11 is an example of a possible aircraft output display on an aircraft that uses the method, system and apparatus of the present invention.

Monitoring Display:

FIG. 11 provides an embodiment of a system output display 1110, which might constitute part of an aircraft multi-sensor contamination monitoring system that employs the present invention. The system includes a dial for debris particle count 1125, a dial for debris size 1130, and a three part gauge that breaks down the particle count to ferrous 1140, metallic non-ferrous 1150 and non-metallic 1160. The system also includes a dial for oxidation 1180 and a dial for water saturation 1170 from the oil quality sensor.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for monitoring and analyzing the condition of a fluid flow comprising the steps of:
    a. separating particulate matter from a primary fluid flow channel;
    b. directing objects in the fluid flow to a sensor array so that the objects pass-along a predetermined path in a substantially still portion of the fluid of the fluid flow;
    c. interrogating a predetermined field of view along the predetermined path with a plurality of partially focused ultrasonic pulses directed along an axis of transmission at an oblique angle to said predetermined path and receiving reflections of ultrasonic pulses from the objects wherein said reflections of ultrasonic pulses are on an axis of reception congruent with the axis of transmission of said ultrasonic pulses;
    d. generating an inductive field along said predetermined path;
    e. distinguishing air bubbles from particulate matter among the objects detected based on a received plurality of reflections;
    f. determining a size of the objects;
    g. determining if the particle is metallic or non-metallic by combining readings from the ultrasonic reflections and inductive field readings; and
    h. determining if a metallic particle is ferrous or non-ferrous from the inductive field readings.

2. The method of claim 1 comprising the further step of determining the condition of the fluid.

3. The method of claim 1 wherein said fluid flowing being monitored is selected from a group of fluids consisting of: beer, wine, milk, ice cream, water, soda, coffee, espresso, chocolate and cocoa.

4. The method of claim 2 wherein the step of determining the condition of the fluid is selected from a group consisting of: the moisture content of the fluid, the oxidation of the fluid, and the size of carbon dioxide bubbles in the fluid.

5. The method of claim 2 wherein the step of determining the condition of the fluid is done with a polymer matrix sensor.

* * * * *